(12) United States Patent (10) Patent No.: US 7,410,993 B2
Mehta et al. (45) Date of Patent: Aug. 12, 2008

(54) 3,6-DISUBSTITUTED AZABICYCLO [3.1.0] HEXANE DERIVIATIVES USEFUL AS MUSCARINIC RECEPTOR ANTAGONISTS

(75) Inventors: Anita Mehta, Plainfield, IL (US); Arundutt V. Silamkoti, Secunderabad (IN); Miriyala Bruhaspathy, Andhra Pradesh (IN); Jang Bahadur Gupta, Dusseldorf (DE)

(73) Assignee: Ranbaxy Laboratories Limited, Gurgaon (IN)

( * ) Notice: Subject to any disclaimer, the term of this patent is extended or adjusted under 35 U.S.C. 154(b) by 16 days.

(21) Appl. No.: 10/524,081

(22) PCT Filed: Aug. 9, 2002

(86) PCT No.: PCT/IB02/03167

§ 371 (c)(1),
(2), (4) Date: Feb. 24, 2006

(87) PCT Pub. No.: WO2004/014363

PCT Pub. Date: Feb. 19, 2004

(65) Prior Publication Data

US 2006/0142371 A1 Jun. 29, 2006

(51) Int. Cl.
*A61K 31/403* (2006.01)
*C07D 209/52* (2006.01)
(52) U.S. Cl. .................... 514/412; 548/515; 548/452
(58) Field of Classification Search ............... 548/515; 514/412
See application file for complete search history.

(56) References Cited

U.S. PATENT DOCUMENTS

| 3,176,019 | A |   | 3/1965  | Campbell et al. | 260/293.4 |
| 4,183,857 | A |   | 1/1980  | Kollmeyer       | 260/326.5 |
| 5,281,601 | A |   | 1/1994  | Cross et al.    | 514/320   |
| 5,948,792 | A |   | 9/1999  | Tsuchiya et al. | 514/317   |
| 6,130,232 | A |   | 10/2000 | Mase et al.     | 514/318   |
| 6,174,900 | B1|   | 1/2001  | Okada et al.    | 514/317   |
| 6,191,165 | B1| * | 2/2001  | Ognyanov et al. | 514/523   |

FOREIGN PATENT DOCUMENTS

| EP | 0 325 571  | 7/1989  |
| EP | 0 388 054  | 9/1990  |
| EP | 0 801 067  | 10/1997 |
| GB | 940540     | 10/1963 |
| JP | 92921/1994 | 4/1994  |
| JP | 135989/1994| 5/1995  |
| WO | WO 89/06644| 7/1989  |
| WO | WO 91/09013| 6/1991  |
| WO | WO 93/16018| 8/1993  |
| WO | WO 93/16048| 8/1993  |
| WO | WO 96/33973| 10/1996 |
| WO | WO 97/45414| 12/1997 |
| WO | WO 98/05641| 2/1998  |
| WO | WO 98/29402| 7/1998  |

OTHER PUBLICATIONS

Morissette et al. Advanced Drug Delivery Reviews 2004, 56, 275-300.*
Wess et al. Life Sciences 2003, 72, 2047-2054.*
O'Neill, M. Drug Discovery Today Oct. 2005, 10(20), 1338.*
Michel et al. Naunyn-Schmiedeberg's Arch Pharmacol 2006, 374, 79-85.*
Latifpour et al. The Journal of Pharmacology and Experimental Therapeutics 1989, 249(1), 81-88.*
Carrier et al. The Journal of Pharmacology and Experimental Therapeutics 1987, 242(2), 531-535.*
Ahren et al. Diabetologia 1996, 39, 383-390.*
Abrams et al. British Journal of Pharmacology 2006, 148, 565-578.*
Kubo et al., "Cloning, sequencing and expression of complementary DNA encoding the muscarinic acetylcholine receptor", *Nature*, 323(2):411-416 (1986).
Bonner et al., "Identification of a Family of Muscarinic Acetylcholine Receptor Genes", *Science*, 237:527-531 (1987).
Eglen et al., "Muscarinic receptor ligands and their theraputic potential", *Current Opinion in Chemical Biology*, 3:426-432 (1999).
Eglen et al., "Theraputic opportunities from muscarinic receptor research", *Trends in Pharmacological Sciences*, 22(8):490-414 (2001).
Felder et al., "Theraputic Opportunities for Muscarinic Receptors in the Central Nervous System", *Journal of Medicinal Chemistry*, 43(23):4333-4353 (2000).
Broadley and Kelly, "Muscarinic Receptor Agonists and Antagonists", *Molecules*, 6:142-193 (2001).
Birdsall et al., "Muscarinic receptors: it's a knockout", *Trends in Pharmacological Sciences*, 22(5):215-219 (2001).
de Groat and Yoshimura, "Pharmacology of the Lower Urinary Tract", *Annual Review of Pharmacology and Toxicology*, 41:691-721 (2001).
Steers, "The future direction of neuro-urology drug research", *Current Opinion in CPNS Investigational Drugs*, 2(3):268-282, 2000.
Chapple, "Muscarinic receptor antagonists in the treatment of overactive bladder", *Urology*, 55(Suppl. 5A):33-46 (2000).
Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).

(Continued)

*Primary Examiner*—Rebecca L Anderson
*Assistant Examiner*—Jason M Nolan
(74) *Attorney, Agent, or Firm*—Jayadeep R. Deshmukh, Esq.; George E. Heibel Esq.

(57) ABSTRACT

This invention generally relates to the derivatives of 3,6 disubstituted azabicyclo[3.1.0] hexanes. The compounds of this invention are muscarinic receptor antagonists which are useful, inter-alia, for the treatment of various diseases of the respiratory, urinary and gastrointestinal systems mediated through muscarinic receptors. The invention also relates to a process for the preparation of the compounds of the present invention, pharmaceutical compositions containing the compounds of the present invention and the methods for treating the diseases mediated through muscarinic receptors.

10 Claims, No Drawings

OTHER PUBLICATIONS

Sagara et al., "Cyclohexylmethylpiperidinyltriphenylpropioamide: A Selective Muscarinic $M_3$ Antagonist Discriminating against the Other Receptor Subtypes", *Journal of Medicinal Chemistry*, 45:984-987 (2002).

Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).

Cheng and Prusoff, "Relationship between the inihibition constant ($KI$) and the concentration of inhibitor which causes 50 per cent inhibition ($I50$) of an enzymatic reaction", *Biochemical Pharmacology*, 22:3099-3108 (1973).

* cited by examiner

3,6-DISUBSTITUTED AZABICYCLO [3.1.0] HEXANE DERIVIATIVES USEFUL AS MUSCARINIC RECEPTOR ANTAGONISTS

FIELD OF THE INVENTION

This invention generally relates to the derivatives of 3,6 disubstituted azabicyclo[3.1.0]hexanes.

The compounds of this invention are muscarinic receptor antagonists which are useful, inter-alia, for the treatment of various diseases of the respiratory, urinary and gastrointestinal systems mediated through muscarinic receptors.

The invention also relates to a process for the preparation of the compounds of the present invention, pharmaceutical compositions containing the compounds of the present invention and the methods for treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cerebral cortex and autonomic ganglia, the $M_2$ subtype is present mainly in the heart where it mediates cholinergically induced bradycardia, and the $M_3$ subtype is located predominantly on smooth muscle and salivary glands (*Nature* 1986; 323: 411; Science, 1987; 237: 527).

A review in Current opinions in Chemical Biology, 1999; 3: 426, as well as in Trends in Pharmacological Sciences, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in J. Med. Chem., 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in Molecules, 2001, 6: 142.

N. J. M. Birdsall et. al. in Trends in Pharmacological Sciences, 2001; 22: 215 have also summarized the recent developments on the role of different muscarinic receptor subtypes using different muscaranic receptor of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of Pharmacological Toxicol., 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in Curr. Opin. Invest. Drugs, 2: 268, C. R. Chapple et. al. in Urology, 55: 33), Steers W D, Barrot D M, Wein A J, 1996, Voiding dysfunction: diagnosis classification and management. In Adult and Pediatric Urology, ed. J Y Gillenwatter, J T Grayhack, S S Howards, J W Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and W096/33973 are other close art references.

A report in J. Med. Chem., 2002; 44:984, describes cyclohexylmethyl piperidinyl triphenylpropioamide derivatives as selective $M_3$ antagonist discriminating against the other receptor subtypes.

SUMMARY OF THE INVENTION

The present invention provides 3,6-disubstituted azabicyclo[3.1.0]hexanes as muscarinic receptor antagonists which are useful as safe and effective therapeutic or prophylactic agents for the treatment of various diseases of the respiratory, urinary and gastrointestinal systems, and process for the synthesis of the compounds.

The invention also provides pharmaceutical compositions containing the compounds together with acceptable carriers, excipients or diluents which are useful for the treatment of various diseases of the respiratory, urinary and gastrointestinal systems.

The present invention also includes within its scope prodrugs of the compounds. In general, such prodrugs will be functionalized derivatives of these compounds which readily get converted in vivo into the defined compounds. Conventional procedures for the selection and preparation of suitable prodrugs are known to the artisan skilled in the art.

The invention also includes the enantiomers, diastereomers, polymorphs, pharmaceutically acceptable salts, pharmaceutically acceptable solvates, esters, N-oxides and metabolites of these compounds having the same type of activity.

The invention further includes pharmaceutical compositions comprising the compounds of the present invention, their enantiomers, diastereomers, prodrugs, polymorphs, pharmaceutically acceptable solvates, esters, N-oxides or metabolites, in combination with a pharmaceutically acceptable carrier and optionally included excipients.

Other advantages of the invention will be set forth in the description which follows, and in part will be apparent from the description or may be learnt by the practice of the invention. The objects and the advantages of the invention may be realized and obtained by means of the mechanisms and combinations pointed out in the appended claims.

In accordance with one aspect of the present invention, there is provided a compound having the structure of Formula I:

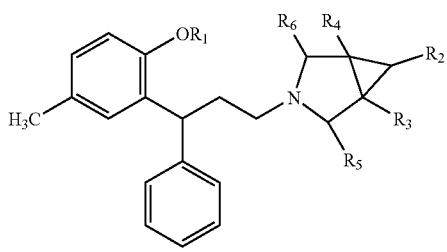

FORMULA-I and its pharmaceutically acceptable salts, pharmaceutically acceptable solvates, esters, enantiomers, diastereomers, N-oxides, polymorphs, prodrugs, metabolites, wherein $R_1$ represents hydrogen, lower ($C_1$-$C_4$) alkyl, lower perhaloalkyl ($C_1$-$C_4$), aryl, aralalkyl;

$R_2$ represents hydrogen, lower ($C_1$-$C_4$) alkyl, lower perhaloalkyl ($C_1$-$C_4$), aralkyl, alkylamino, alkoxyalkyl, alkoxyaryl, alkoxycarbonyl;

$R_3$, $R_4$, $R_5$ and $R_6$ independently represent hydrogen, lower ($C_1$-$C_4$) alkyl, lower perhaloalkyl ($C_1$-$C_4$), cyano, hydroxy, nitro, lower alkoxycarbonyl, halogen (e.g., F, Cl, Br, I), lower alkoxy ($C_1$-$C_4$), lower perhaloalkoxy ($C_1$-$C_4$), amino or lower alkylamino.

In accordance with a second aspect of the present invention, there is provided a method for treatment or prophylaxis of an animal or human suffering from a disease or disorder of the respiratory, urinary and gastrointestinal systems, wherein the disease or disorder is mediated through muscarinic receptors.

In accordance with a third aspect of the present invention, there is provided a method for treatment or prophylaxis of an animal or human suffering from a disease or disorder associated with muscarinic receptors, comprising administering to a patient in need thereof, an effective amount of muscarinic receptor antagonist compounds as described above.

In accordance with a fourth aspect of the present invention, there is provided a method for treatment or prophylaxis of an animal or human suffering from a disease or disorder of the respiratory system such as bronchial asthma, chronic obstructive pulmonary disorders (COPD), pulmonary fibrosis, etc.; urinary system which induce such urinary disorders as urinary incontinence, lower urinary tract symptoms (LUTS) etc.; and gastrointestinal system such as irritable bowel syndrome, obesity, diabetes and gastro intestinal hyperkinesis with compounds as described above, wherein the disease or disorder is associated with muscarinic receptors.

In accordance with a fifth aspect of the present invention, there are provided processes for preparing the compounds as described above.

The compounds of the present invention are novel and exhibit significant potency in terms of their activity, which was determined by in vitro receptor binding and functional assays and in vivo experiments using anaesthetized rabbit. The compounds that were found active in in vitro assay were tested in vivo. Some of the compounds of the present invention were found to be potent muscarinic receptor antagonists with high affinity towards $M_3$ receptors. Therefore, the present invention provides the pharmaceutical compositions for the possible treatment from the disease or disorders associated with muscarinic receptors. In addition the compounds of the present invention can be administered orally or parenterally.

DETAILED DESCRIPTION OF THE INVENTION

The compounds of Formula I of the present invention may be prepared by the reaction sequence as shown in Scheme I. The preparation comprises condensing a compound of Formula II with the compound of Formula III wherein $R_2$ represents hydrogen, lower ($C_1$-$C_4$) alkyl, lower perhaloalkyl ($C_1$-$C_4$), aralkyl, alkylamino, alkoxyalkyl, alkoxyaryl, alkoxycarbonyl;

$R_3$, $R_4$, $R_5$ and $R_6$ independently represent hydrogen, lower ($C_1$-$C_4$) alkyl, lower perhaloalkyl ($C_1$-$C_4$), cyano, hydroxy, nitro, lower alkoxycarbonyl, halogen (e.g., F, Cl, Br, I), lower alkoxy ($C_1$-$C_4$), lower perhaloalkoxy ($C_1$-$C_4$), amino or lower alkylamino;

and $R_7$ is any leaving group known in the art and is preferably selected from halogen (F, Cl, Br or I), O-tosyl, O-mesityl.

The condensation is carried out in the presence of a condensing agent which is an organic or inorganic base selected from the group consisting of potassium carbonate, sodium carbonate, triethylamine and diisopropylamine in a suitable solvent or a mixture of solvents. The solvents are selected from the group consisting of dimethylformamide, dimethylacetamide, toluene and acetonitrile, to give a protected compound of Formula IV wherein $R_2$, $R_3$, $R_4$, $R_5$ and $R_6$ have the same meaning as defined earlier. The compound of Formula IV is further deprotected in the presence of deprotecting agent which is preferably palladium on carbon, to give a compound of Formula V (Formula I, when $R_1$ is hydrogen).

Scheme-I

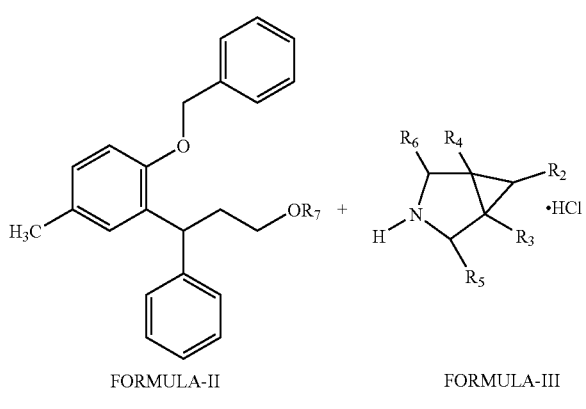

-continued

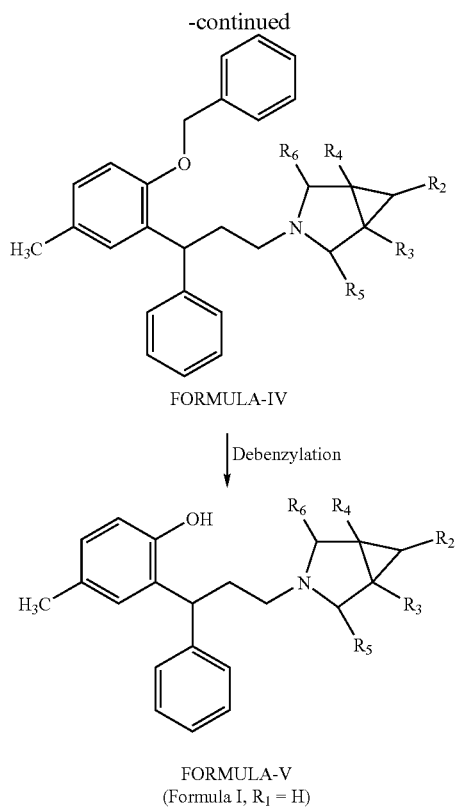

FORMULA-IV

↓ Debenzylation

FORMULA-V
(Formula I, R₁ = H)

In the above scheme, where specific bases, condensing agents, deprotecting agents, solvents, etc. are mentioned, it is to be understood that other bases, condensing agents, deprotecting agents, solvents, etc. known to those skilled in the art may be used. Similarly, the reaction temperature and duration may be adjusted according to the desired needs.

An illustrative list of particular compounds according to the invention and capable of being produced by Scheme I include:

| Compound No. | Chemical Name |
|---|---|
| 1. | 1-(3-azabicyclo[3.1.0]hex-3-yl)-3-(2-benzyloxy-5-methylphenyl)-3-phenyl propane (Compound No. 1), |
| 2. | 1-(3-azabicyclo[3.1.0]hex-3-yl)-3-(2-hydroxy-5-methylphenyl)-3-phenyl propane (Compound No. 2), |
| 3. | 1-(1,5-dimethyl-3-azabicyclo[3.1.0]hex-3-yl)-3-(2-benzyloxy-5-methylphenyl)-3-phenyl propane (Compound No. 3), |
| 4. | 1-(1,5-dimethyl-3-azabicyclo[3.1.0]hex-3-yl)-3-(2-hydroxy-5-methylphenyl)-3-phenyl propane (Compound No. 4), |
| 5. | 1-(1-methyl-3-azabicyclo[3.1.0]hex-3-yl)-3-(2-benzyloxy-5-methylphenyl)-3-phenyl propane (Compound No. 5), |
| 6. | 1-(1-methyl-3-azabicyclo[3.1.0]hex-3-yl)-3-(2-hydroxy-5-methylphenyl)-3-phenyl propane (Compound No. 6), |
| 7. | 1-(2-methyl-3-azabicyclo[3.1.0]hex-3-yl)-3-(2-benzyloxy-5-methylphenyl)-3-phenyl propane (Compound No. 7), |
| 8. | 1-(2-methyl-3-azabicyclo[3.1.0]hex-3-yl)-3-(2-hydroxy-5-methylphenyl)-3-phenyl propane (Compound No. 8), |
| 9. | 1-(2-methyl-3-azabicyclo[3.1.0]hex-3-yl)-3-(2-hydroxy-5-methylphenyl)-3-phenyl propane (Compound No. 9). |

The illustrated list of the compounds is also given in Table-I:

TABLE 1

(Formula-1)

| Compound No. | $R_1$ | $R_2$ | $R_3$ | $R_4$ | $R_5$ | $R_6$ |
|---|---|---|---|---|---|---|
| 1 | benzyl | H | H | H | H | H |
| 2 | H | H | H | H | H | H |
| 3 | benzyl | H | $CH_3$ | $CH_3$ | H | H |
| 4 | H | H | $CH_3$ | $CH_3$ | H | H |
| 5 | benzyl | H | $CH_3$ | H | H | H |
| 6 | H | H | $CH_3$ | H | H | H |
| 7 | benzyl | H | H | H | $CH_3$ | H |
| 8 | H | H | H | H | $CH_3$ | H |
| 9 | H | H | H | H | $CH_3$ | H |

These compounds have selective antagonistic activity against muscarinic $M_3$ receptors and can hence be used safely with minimum side effects.

Because of their valuable pharmacological properties, the compounds of the present invention may be administered to an animal for treatment orally, or by parenteral route. The pharmaceutical compositions of the present invention are preferably produced and administered in dosage units, each unit containing a certain amount of at least one compound of the invention and/or at least one physiologically acceptable salt addition thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The examples mentioned below demonstrate the general synthetic procedure as well as the specific preparation of the preferred compound. The examples are given to illustrate the details of the invention and should not be construed to limit the scope of the invention.

EXAMPLE-1

Preparation of 1-(3-azabicyclo[3.1.0]hex-3-yl)-3-(2-benzyloxy-5-methylphenyl)-3-phenyl propane (Compound No.1)

A solution of 3-(2-benzyloxy-5-methylphenyl)-3-phenyl-propyl-p-toluene sulphonate (Prepared by following the process as described in EP 0 325 571, 0.486 gm, 1 mmol), 3-azabicyclo[3.1.0]hexane hydrochloride (Prepared by following the process as described in U.S. Pat. No. 4,183,857, 0.12 gm, 1 mmol), potassium carbonate (0.275 gm, 2 mmol), potassium iodide (0.17 gm, 1 mmol) in acetonitrile (10 ml) and dimethylformamide (10 ml) were refluxed for 15 hours at about 100° C. The cooled reaction mixture was poured into water and extracted with ethyl acetate. The combined organic layers were dried over sodium sulphate and concentrated in vacuo to afford an oily residue, which was purified by column chromatography (silica gel 100-200 mesh), eluting the compound with 50-50 ethylacetate-hexane mixture.

$^1$H-NMR (CDCl$_3$) δ values: 7.36-6.73 (m, arom, 13H), 4.97-4.95 (d, 2H), 4.43 (t, 1H), 2.99 (d, 2H), 2.35-2.13 (m, 9H), 0.88 (m, 2H), 0.67 (m, 1H), 0.07 (m, 1H)

EXAMPLE-2

Preparation of 1-(3-azabicyclo[3.1.0]hex-3-yl)-3-(2-hydroxy-5-methylphenyl)-3-phenyl propane (Compound No.2)

The compound of Example 1, in methanol (50 ml) was added to a suspension of palladium over carbon (wet) and subjected to hydrogenation in parr apparatus at 45 psi for 5 hours. The reaction mixture was filtered and the filterate was concentrated in vacuo to afford an oily residue which was purified by column chromatography (silica gel 100-200 mesh), eluting the compound with 20-80, ethylacetate-hexane mixture.

$^1$H-NMR (CDCl$_3$) δ-values: 7.31-6.83 (m, arom, 8H), 6.44 (s, 1H), 4.44-4.4 (m, 1H), 3.26-3.10 (dd, 2H), 2.63-2.29 (m, 6H), 2.08 (s, 3H), 1.48-1.44(m, 2H), 0.78 (m, 1M), 0.56 (m, 1H)

EXAMPLE-3

Preparation of 1-(1,5-dimethyl-3-azabicyclo[3.1.0]hex-3-yl)-3-(2-benzyloxy-5-methylphenyl)-3-phenyl propane (Compound No.3)

This compound was synthesized by following the procedure described in Example-1, using 1,5-dimethyl-3-azabicyclo[3.1.0]hexane hydrochloride, (Synthesized as per reported procedure of U.S. Pat. No. 4,183,857, using methyl methacrylate and ethyl 2-chloropropionate instead of ethyl acrylate and ethyl chloroacetate) instead of 3-azabicyclo[3.1.0]hexane. (m.p. 93-95° C.)

$^1$H-NMR (CDCl$_3$) δ-values: 7.38-6.79 (m, arom, 13H), 5.07-4.97 (dd, 2H), 4.51 (t, 1H), 3.02 (d, 2H), 2.38-2.07 (m, 6H), 1.72 (s, 3H), 1.10 (s, 6H), 0.94 (m, 1H, 0.06 (m,

EXAMPLE-4

Preparation of 1-(1,5-dimethyl-3-azabicyclo[3.1.0]hex-3-yl)-3-(2-hydroxy-5-methylphenyl)-3-phenyl propane (Compound No.4)

This compound was synthesized by following the procedure described in Example-2, using compound prepared in Example 3 as the starting material.

$^1$H-NMR (CDCl$_3$) δ values: 7.34-6.79 (m, arom, 8H), 6.42 (s, 1H), 4.45-4.4 (m, 1H), 3.22-3.08 (dd, 2H), 2.34-2.0 (m, 9H), 1.11 (s, 6H), 0.88 (m, 1H), 0.18 (m, 1H)

EXAMPLE-5

Preparation of 1-(1-methyl-3-azabicyclo[3.1.0]hex-3-yl)-3-(2-benzyloxy-5-methylphenyl)-3-phenyl propane (Compound No.5)

This compound was synthesized by following the procedure described in Example-1, using 1-methyl-3-azabicyclo[3.1.0]hexane hydrochloride (Synthesized as per reported procedure of U.S. Pat. No. 4,183,857, using ethyl 2-chloropropionate instead of ethyl chloroacetate) instead of 3-azabicyclo[3.1.0]hexane. (m.p. 74.9-76° C.)

$^1$H-NMR (CDCl$_3$) δ-values: 7.33-6.73 (m, arom, 13H), 4.96-4.95 (d, 2H), 4.47-4.42 (t, 1H), 2.92-2.89 (d, 2H), 2.32-2.03 (m, 6H), 1.59 (s, 3H), 1.16 (s, 3H), 0.95-0.94 (m, 1H), 0.84-0.83 (m, 1H), 0.21 (m, 1H)

EXAMPLE-6

Preparation of 1-(1-methyl-3-azabicyclo[3.1.0]hex-3-yl)-3-(2-hydroxy-5-methylphenyl)-3-phenyl propane (Compound No.6)

This compound was synthesized by following the procedure described in Example-2, using compound prepared in Example 5 as the starting material.

$^1$H-NMR (CDCl$_3$) δ-values: 7.34-7.2 (m, arom, 8H), 6.42 (s, 1H), 4.4-4.39 (m, 1H), 3.2-3.04 (dd, 2H), 2.31-2.16 (m, 6H), 2.07 (s, 3H), 1.25 (s, 3H), 1.23 (m, 1H), 0.95-0.92 (m, 1H), 0.45 (m, 1H)

EXAMPLE-7

Preparation of 1-(2-methyl-3-azabicyclo[3.1.0]hex-3-yl)-3-(2-benzyloxy-5-methylphenyl)-3-phenyl propane (Compound No.7)

Step a: Preparation of 3-benzyl-4-hydroxy-4-methyl-3-azabicyclo[3.1.0]hexan-2-one 3-benzyl-3-azabicyclo[3.1.0]hexane-2,4-dione(U.S. Pat. No. 4,183,857, 1.9 gm, 9.5 mmol) was dissolved in 100 ml of tetrahydrofuran and cooled to −78° C. Methyllithium (10.5 ml of a 0.98M solution in ether, 10.2 mmol) was added dropwise. Saturated aqueous ammonium chloride was added to the cold reaction mixture; the mixture was then extracted with ethyl acetate. The combined organic layers were dried over sodium sulphate, filtered and concentrated in vacuo to provide the title compound.

$^1$H-NMR (CDCl$_3$) δ values: 7.28-7.17 (m, 5H), 4.63-4.58 (d, 1H), 4.24-4.18 (d, 1H), 3.01 (s, 1H), 2.16-2.03 (m, 2H), 1.25 (s,3H), 0.80 (m, 1H), 0.65 (m, 1H), IR (KBr): 1655 cm$^{-1}$ (carbonyl).

Step b: Preparation of 3-benzyl-2-methyl-3-azabicyclo[3.1.0]hexane

A solution of the title compound of preparation step a (1.5 gm, 7 mmol) in tetrahydrofuran (100 ml); treated with lithium aluminium hydride (0.8 gm, 21 mmol) and heated to reflux for 16 hrs. The cold reaction mixture was then treated with saturated ammonium chloride in water, precipitated solids were filtered and the filtrate concentrated to afford the title compound as an oily residue.

$^1$H-NMR (CDCl$_3$) δ-values: 7.31-7.19 (m, 5H), 3.9-3.87 (d, 1H), 3.18-3.14 (d, 1H), 2.89-2.86 (d, 1H), 2.69 (m, 1H), 2.33-2.29 (m, 1H), 1.35-1.21 (m, 2H), 1.14-1.12 (d, 3H), 0.73-0.71 (m, 1H), 0.19-0.18 (m, 1H).

IR (DCM): 1637 cm$^{-1}$

Step c: Preparation of 2-methyl-3-azabicyclo[3.1.0]hexane hydrochloride

The compound of step b (1.0 gm) was dissolved in methanol (50 ml) and treated with palladium on charcoal (10% by weight, 0.2 gm) and subjected to parr hydrogenation at 45 psi for 6 hrs. The reaction mixture was then filtered and the filterate acidified with concentrated hydrochloric acid, the solvents were evaporated to afford the title compound.

$^1$H-NMR (CDCl$_3$) δ values: 3.91 (b, 1H), 3.49-3.44 (m, 2H), 1.66-1.63 (m, 2), 1.53-1.51 (d, 3H), 1.02-0.97 (m, 1H), 0.73-0.65 (m, 1H).

Step d: Preparation of 1-(2-methyl-3-azabicyclo [3.1.0]hex-3-yl)-3-(2-benzyloxy-5-methylphenyl)-3-phenyl propane This compound was synthesized by following the procedure described in Example-1, using 2-methyl-3-azabicyclo[3.1.0]hexane hydrochloride instead of 3-azabicyclo[3.1.0]hexane.

$^1$H-NMR (CDCl$_3$) δ-values: 7.32-6.7 (m, arom, 13H), 4.96-4.93 (d, 2H), 4.46-4.4 (t, 1H), 3.12-3.08 (m, 1H), 2.42-2.04 (m, 9H), 1.61 (s, 3H), 0.89-0.86 (m, 2H), 0.64-0.63 (m, 1H), 0.16-0.15 (m, 1H)

EXAMPLE-8

Preparation of 1-(2-methyl-3-azabicyclo[3.1.0]hex-3-yl)-3-(2-hydroxy-5-methylphenyl)-3-phenyl propane (Compound No.8)

This compound was synthesized by following the procedure described in Example-2, using compound prepared in Example 7 as the starting material. It was purified by column chromatography on a 100×200 mesh size silica gel using 10-90 ethyl acetate-hexane as eluent (semi solid).

$^1$H-NMR (CDCl$_3$) δ-values: 7.37-6.79 (m, arom, 8H), 6.45 (s, 1H), 4.48-4.42 (m, 1H), 3.33-3.30 (d, 2H), 2.65-2.02 (m, 9H), 1.45 (s, 3H), 1.14 (m, 1H), 0.77 (m, 1H),

EXAMPLE -9

Preparation of 1-(2-methyl-3-azabicyclo[3.1.0]hex-3-yl)-3-(2-hydroxy-5-methylphenyl)-3-phenyl propane (Compound No.9)

This compound was eluted by the column chromatography of the above reaction as in Example-8, by using 20-80 ethylacetate-hexane as eluent.

$^1$H-NMR (CDCl$_3$) δ-values: 7.37-6.79 (m, arom, 8H), 6.45 (s, 1H), 4.48-4.42 (m, 1H), 3.33-3.30 (d, 1H), 2.65-1.1 (m, 14H), 0.77 (m, 1H), 0.4 (m, 1H).

Pharmacological Testing Results

Radioligand Binding Assays:

The affinity of test compounds for $M_2$ and $M_3$ muscarinic receptor subtypes was determined by [$^3$H]-N-methylscopolamine binding studies using rat heart and submandibular gland, respectively as described by Moriya et al., (Life Sci, 1999,64(25):2351) with minor modifications.

Membrane preparation: Submandibular glands and heart were isolated and placed in ice cold homogenizing buffer (HEPES 20 mM, 10 mM EDTA, pH 7.4) immediately after sacrifice. The tissues were homogenized in 10 volumes of homogenizing buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at –70° C. until the time of assay.

Ligand binding assay: The compounds were dissolved and diluted in DMSO. The membrane homogenates (150-250 μg protein) were incubated in 250 μl of assay buffer (HEPES 20 mM, pH 7.4) at 24-25° C. for 3 hours. Non-specific binding was determined in the presence of 1 μM atropine. The incubation was terminated by vacuum filtration over GF/B fiber filters(Wallac). The filters were then washed with ice cold 50 mM Tris HCl buffer (pH 7.4). The filter mats were dried and bound radioactivity retained on filters was counted. The $IC_{50}$ & Kd were estimated by using the non-linear curve fitting program using G Pad Prism software. The value of inhibition constant Ki was calculated from competitive binding studies by using Cheng & Prusoff equation (*Biochem Pharmacol*, 1973;22: 3099), Ki=$IC_{50}$/(1+L/Kd), where L is the concentration of [$^3$H]NMS used in the particular experiment.

Functional Experiments Using Isolated Rat Bladder:

Methodology:

Animals were euthanized by overdose of urethane and whole bladder was isolated and removed rapidly and placed in ice cold Tyrode buffer with the following composition (mMol/L) NaCl 137; KCl 2.7; $CaCl_2$ 1.8; $MgCl_2$ 0.1; $NaHCO_3$ 11.9; $NaH_2PO_4$ 0.4; Glucose 5.55 and continuously gassed with 95% $O_2$ and 5% $CO_2$.

The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period the stabilization of the tissue contractile response was assessed with 1 μMol/L of Carbachol consecutively for 2-3 times. Subsequently a cumulative concentration response curve to carbachol ($10^{-9}$ mol/L to $3\times10^{-5}$ mol/L) was obtained. After several washes, once the baseline was achieved, cumulative concentration response curve was obtained in presence of NCE (NCE added 20 min. prior to the second CRC).

The contractile results were expressed as % of control E max. ED50 values were calculated by fitting a non-linear regression curve (Graph Pad Prism). pKB values were calculated by the formula pKB=–log [(molar concentration of antagonist/(dose ratio-1))]

where,
dose ratio=ED50 in the presence of antagonist/ED50 in the absence of antagonist.

The results are listed in Table II

In-Vitro Tests

TABLE II

| | Receptor Binding Assay Ki (nM) | | | Functional Assay |
|---|---|---|---|---|
| | $M_2$ | $M_3$ | Selectivity | $K_B$ |
| Compound No. 1 | >10,000 | >1000 | — | — |
| Compound No. 2 | 105 | 50 | 2.1 | 8.19 |
| Compound No. 3 | >10,000 | >10,000 | — | — |
| Compound No. 4 | >1000 | >1000 | — | — |
| Compound No. 6 | 221 | 118 | 1.87 | — |
| Compound No. 7 | >10,000 | >1000 | — | — |
| Compound No. 8 | 34 | 79 | 0.43 | 8.39 |
| Compound No. 9 | 42 | 25 | 1.68 | 8.49 |
| Tolterodine | 6.91 | 7.07 | 0.98 | 2.0 |
| Oxybutynin | 6.97 | 0.95 | 7.34 | 2.0 |
| Atropine | 0.5 | 0.6 | 0.83 | |

While the present invention has been described in terms of its specific embodiments, certain modifications and equivalents will be apparent to those skilled in the art and are intended to be included within the scope of the present invention.

We claim:

1. A compound having the structure of Formula I:

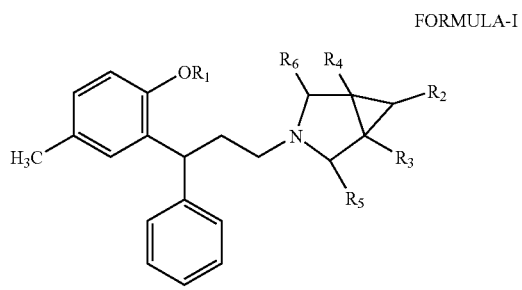

FORMULA-I and its pharmaceutically acceptable salts, pharmaceutically acceptable enantiomers, diastereomers or N-oxides, wherein
$R_1$ represents hydrogen, lower ($C_1$-$C_4$) alkyl, lower perhaloalkyl ($C_1$-$C_4$), aryl or aralkyl;
$R_2$ represents hydrogen, lower ($C_1$-$C_4$) alkyl, lower perhaloalkyl ($C_1$-$C_4$), aralkyl, alkylamino, alkoxyalkyl, alkoxyaryl or alkoxycarbonyl; and
$R_3$, $R_4$, $R_5$ and $R_6$ independently represent hydrogen, lower ($C_1$-$C_4$) alkyl, lower perhaloalkyl ($C_1$-$C_4$), cyano, hydroxy, nitro, lower alkoxycarbonyl, halogen (e.g., F, Cl, Br, I), lower alkoxy ($C_1$-$C_4$), lower perhaloalkoxy ($C_1$-$C_4$), amino or lower alkylamino.

2. A compound selected from the group consisting of:
1-(3-azahicyclo[3.1.0]hex-3-yl)-3-(2-benzyloxy-5-methylphenyl)-3-phenyl propane (Compound No.1),
1-(3-azabicyclo[3.1.0]hex-3-yl)-3-(2-hydroxy-5-methylphenyl)-3-phenyl propane (Compound No.2),
1-(1,5-dimethyl-3-azabicyclo[3.1.0]hex-3-yl)-3-(2-benzyloxy-5-methylphenyl)-3-phenyl propane (Compound No.3),
1-(1,5-dimethyl-3-azabicyclo[3.1.0]hex-3-yl)-3-(2-hydroxy-5-methylphenyl)-3-phenyl propane (Compound No.4),
1-(1-methyl-3-azabicyclo[3.1.0]hex-3-yl)-3-(2-benzyloxy-5-methylphenyl)-3-phenyl propane (Compound No.5),
1-(1-methyl-3-azabicyclo[3.1.0]hex-3-yl)-3-(2-hydroxy-5-methylphenyl)-3-phenyl propane (Compound No.6),
1-(2-methyl-3-azabicyclo[3.1.0]hex-3-yl)-3-(2-benzyloxy-5-methylphenyl)-3-phenyl propane (Compound No.7),
1-(2-methyl-3-azabicyclo[3.1.0]hex-3-yl)-3-(2-hydroxy-5-methylphenyl)-3-phenyl propane (Compound No.8), and
1-(2-methyl-3-azabicyclo[3.1.0]hex-3-yl)-3-(2-hydroxy-5-methylphenyl)-3-phenyl propane (Compound No.9).

3. A pharmaceutical composition comprising a therapeutically effective amount of a compound as defined in claim 1 or 2 together with pharmaceutically acceptable caters, excipients or diluents.

4. A method for treatment of an animal or a human suffering from a disease or disorder of the respiratory, urinary and gastrointestinal systems, wherein the disease or disorder is mediated through muscarinic receptors, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes and gastrointestinal hyperkinesis, the method comprising administering to said mammal or human, a therapeutically effective amount of a compound having the structure of Formula I,

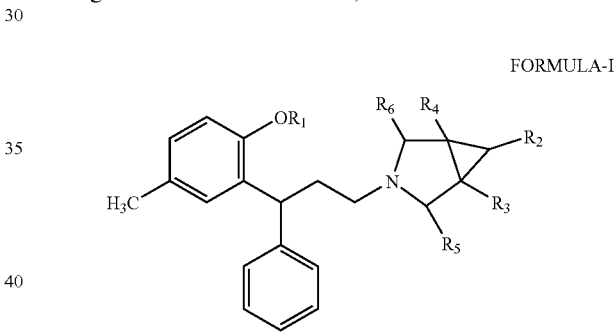

FORMULA-I or its pharmaceutically acceptable salts, pharmaceutically acceptable enantiomers, diastereomers, or N-oxides, wherein
$R_1$ represents hydrogen, lower ($C_1$-$C_4$) alkyl, lower perhaloalkyl ($C_1$-$C_4$), aryl or aralkyl;
$R_2$ represents hydrogen, lower ($C_1$-$C_4$) alkyl, lower perhaloalkyl ($C_1$-$C_4$), aralkyl, alkylamino, alkoxyalkyl, alkoxyaryl or alkoxycarbonyl; and
$R_3$, $R_4$, $R_5$ and $R_6$ independently represent hydrogen, lower ($C_1$-$C_4$) alkyl, lower perhaloalkyl ($C_1$-$C_4$), cyano, hydroxy, nitro, lower alkoxycarbonyl, halogen (e.g., F, Cl, Br, I) lower alkoxy ($C_1$-$C_4$), lower perhaloalkoxy ($C_1$-$C_4$), amino or lower alkylamino.

5. The method for treatment of an animal or a human suffering from a disease or disorder of the respiratory, urinary and gastrointestinal systems, wherein the disease or disorder is mediated through muscarinic receptors, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes and gastrointestinal hyperkinesis, the method comprising administering to said animal or human, a therapeutically effective amount of the pharmaceutical composition according to claim 3.

6. A process of preparing a compound of Formula I,

FORMULA-I

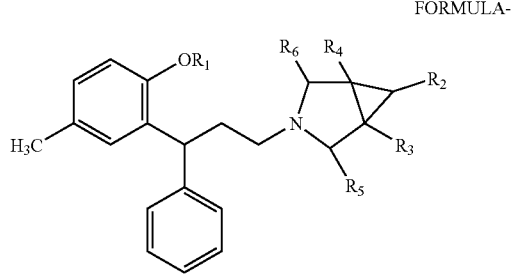

or its pharmaceutically acceptable salts, pharmaceutically acceptable enantiomers, diastereomers, or N-oxides, wherein
$R_1$ represents hydrogen, lower ($C_1$-$C_4$) alkyl, lower perhaloalkyl ($C_1$-$C_4$), aryl or aralkyl;
$R_2$ represents hydrogen, lower ($C_1$-$C_4$) alkyl, lower perhaloalkyl ($C_1$-$C_4$), aralkyl, alkylamino, alkoxyalkyl, alkoxyaryl or alkoxycarbonyl; and
$R_3$, $R_4$, $R_5$ and $R_6$ independently represent hydrogen, lower ($C_1$-$C_4$) alkyl, lower perhaloalkyl ($C_1$-$C_4$), cyano, hydroxy, nitro, lower alkoxycarbonyl, halogen (e.g., F, Cl, Br, I), lower alkoxy ($C_1$-$C_4$), lower perhaloalkoxy ($C_1$-$C_4$), amino or lower alkylamino, said process comprising:
condensing a compound of Formula II with a compound of Formula III

FORMULA-II

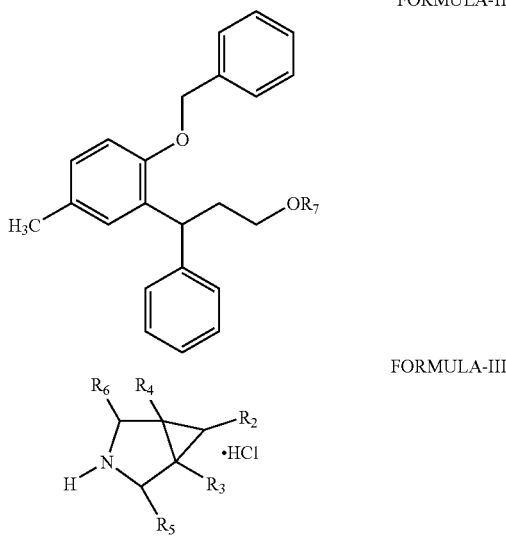

wherein $R_7$ is a leaving group, in the presence of a condensing agent to give a protected compound of Formula IV,

FORMULA-IV

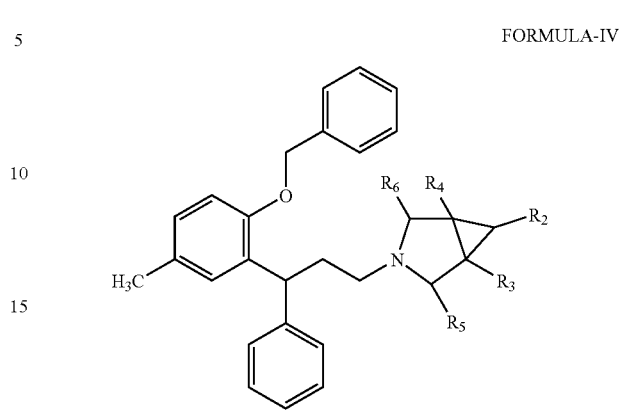

which is further deprotected in the presence of a deprotecting agent to a compound of Formula V (Formula I, $R_1$=hydrogen).

FORMULA-V

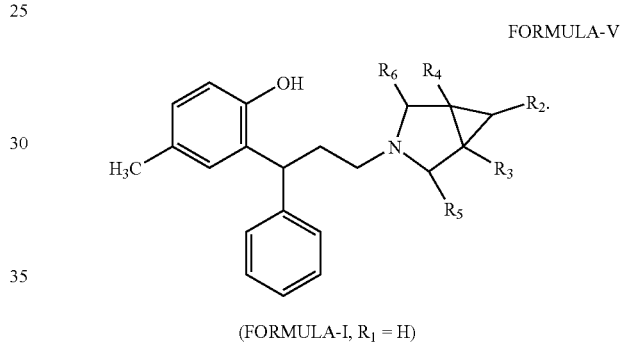

(FORMULA-I, $R_1$ = H)

7. The process according to claim 6 wherein the condensing agent is selected from the group consisting of potassium carbonate, sodium carbonate, triethylamine and diisopropylamine.

8. The process according to claim 6 wherein the condensation of Formula II and Formula III is carried out in the presence of a solvent or a mixture of solvents selected from the group consisting of dimethylformamide, dimethylsulfoxide, toluene and acetonitrile.

9. The process according to claim 6 wherein the leaving group $R_7$ is selected from the group consisting of halogens (F, Cl, Br, I), O-tosyl and O-mestyl group.

10. The process according to claim 6 wherein the deprotecting agent is palladium on carbon.

* * * * *